United States Patent [19]
Howard

[11] Patent Number: 5,431,037
[45] Date of Patent: Jul. 11, 1995

[54] SEDIMENTATION RATE MEASURING DEVICE AND SAMPLER THEREFOR

[75] Inventor: Colin J. Howard, Hornsby, Australia

[73] Assignee: Oscillation Pty Limited, New South Wales, Australia

[21] Appl. No.: 237,181

[22] Filed: May 3, 1994

[30] Foreign Application Priority Data

May 14, 1993 [AU] Australia ............... PL8822

[51] Int. Cl.⁶ .................. G01N 15/04; G01N 1/14
[52] U.S. Cl. ........................ 73/61.68; 73/61.69; 73/864.35; 73/864.81
[58] Field of Search ............ 73/61.68, 61.69, 61.65, 73/64.56, 864.35, 864.81, 864.34

[56] References Cited

U.S. PATENT DOCUMENTS

| | | | |
|---|---|---|---|
| 3,880,011 | 4/1975 | Johnson | 73/864.35 |
| 3,915,011 | 10/1975 | Nelson | 73/864.35 |
| 4,194,391 | 3/1980 | Rosenberger | 73/61.64 |
| 4,267,723 | 5/1981 | Mull | 73/61.65 |
| 4,313,340 | 2/1982 | Schniewind | 73/61.69 |
| 4,318,296 | 3/1982 | Parker et al. | 73/61.68 |

FOREIGN PATENT DOCUMENTS 528273 11/1980 Australia .

Primary Examiner—Hezron E. Williams
Assistant Examiner—Michael J. Brock
Attorney, Agent, or Firm—Michael J. Striker

[57] ABSTRACT

This invention relates to a device and method for the determination of the rate of sedimentation of particles in a liquid and for controlling the addition of a flocculant to the liquid in accordance with the sedimentation rate so determined. The apparatus comprises a sample chamber into which the liquid is drawn and held solely by maintenance of a reduced pressure in the chamber. The rate of sedimentation of the particles is then determined by any suitable means known in the art.

8 Claims, 2 Drawing Sheets

SEDIMENTATION RATE MEASURING DEVICE AND SAMPLER THEREFOR

FIELD OF THE INVENTION

The present invention relates to a device and method for the determination of the rate of sedimentation of particles in a sample of a liquid and controlling the addition of a flocculant to a body of the liquid from which the sample was drawn in accordance with the sedimentation rate so determined.

BACKGROUND ART

There are many occasions in the mining industry, in agriculture and in waste water treatment when it is necessary to separate fine particulate matter from a body of a liquid such as water. This is often achieved by a process of sedimentation or settling. The rate of sedimentation of particles is partly dependent upon their mass and it is therefore advantageous in many cases to add a flocculant to the body of water to induce the fine particles to aggregate or floc together. This increases the mass of the particles and hence their sedimentation rate. As flocculant chemicals are expensive and as there may be adverse environmental effects from excessive flocculant addition it is .desirable to add only sufficient flocculant to the body of liquid to impart the desired rate of sedimentation to the particles in the liquid.

It is known to periodically measure the sedimentation rate of particles in a body of a liquid and to control the rate of addition of the flocculant to the body of liquid in accordance with the rate of sedimentation of the particles. If the particles are not sedimenting fast enough then more flocculant is added. If the particles are settling faster than is required then the addition of flocculant may be slowed down or stopped.

In known devices for the above purpose a sample of the liquid is drawn up into a sample container by the induction of a reduced pressure in the sample container. Once the liquid level in the container has reached a desired level a pinch valve in the lower end of the sample tube is closed and the vacuum applied to the sample container is released. The pinch valve serves to hold the liquid level constant in the sample container until the rate of sedimentation of the particles in the liquid has been determined. The pinch valve is then opened to release the sample from the sample container and to allow it to flow back into the body of the liquid.

It has been considered necessary by those working in the field to use a pinch valve or some similar mechanical valve means to hold the sample in the sample container. This perception is based on the need to hold the level of the liquid in the sample container with absolute certainty. If the level of the sample in the sample container were allowed to drop during the period during which the sedimentation measurement were taking place the accuracy of the measurement would be seriously jeopardised. The use of such a mechanical valve however has a number of disadvantages. It has in fact proven difficult to provide a guaranteed seal in the pinch valve despite substantial efforts over many years to provide a satisfactory mechanical seal. The vibration caused by the opening and closing of the pinch valve have been found to adversely affect electronic control equipment associated with the device. It has also been found that in the field where the valve is required to open and close many times each day for years on end the deterioration of the components of the valve parts present a serious maintenance load.

Australian Patent 528273 describes slurry suspension sampling equipment in which the liquid sample is drawn into a sample chamber and temporarily held at a predetermined level to allow for the measurement of the settling rate of the suspension by a timer means which measures the actual settling period of the suspension between two predetermined levels. After the determination of the settling rate and the consequent adjustment of the flocculent flow control valve, the sample of liquid is discharged from the settling chamber via a discharge pipe located at the lower end of the settling chamber and which is normally held closed by a solenoid operated valve.

The present inventor has found that the presence of a pinch valve or some similar mechanical valve at the bottom of the sample container is, in fact, not necessary. This inventor has surprisingly found that it is possible to hold the sample in the sample container with an acceptable accuracy merely by holding the reduced pressure above the sample for the duration of the period during which the sedimentation rate of particles in the sample is determined, This approach substantially reduces the cost of the device and avoids many of the problems associated with the prior art arrangement.

DISCLOSURE OF THE INVENTION

The present invention consists in a device for the determination of the rate of sedimentation of particles in a sample of a liquid and controlling the addition of a flocculant to the liquid in accordance with the rate of sedimentation so determined, the device comprising a sample container, an inlet duct in fluid communication with the sample container and extending downwardly from a lower end thereof and adapted to extend into a body of liquid to be sampled, suction means in fluid communication with an upper end of the sample container and adapted to create a reduced pressure in the sample container such that a sample of the liquid is drawn into the sample container, means to measure the rate of sedimentation of particles in the liquid sample, flocculant addition means adapted to add flocculant to the body of liquid from which the sample was drawn and means adapted to control the addition of flocculant from the flocculant addition means into the body of liquid in accordance with the rate of sedimentation of the particles in the liquid sample, the device being characterised in that the sample container and the suction means are adapted to hold the sample within the sample container, while the rate of sedimentation of the particles is determined, solely by maintenance of the reduced pressure in the sample container above the liquid sample.

In a further aspect the present invention consists in a process for controlling the sedimentation of particles in a body of a liquid comprising the steps of drawing a sample of the liquid into a sample container through an inlet duct in fluid communication with a lower end of the sample container and with the body of liquid by the creation of a reduced pressure in the sample container, determining the rate of sedimentation of particles in the sample and controlling the addition of flocculant from a flocculant addition means into the body of liquid in accordance with the rate of sedimentation of the particles in the sample, the process being characterised in that the sample is retained in the sample container throughout the determination of the sedimentation rate of particles in the sample solely by maintenance of the reduced pressure in the sample container above the sample.

The device and process according to the invention may be applied to controlling the clarification of water in a wide range of industries including mining, agriculture and sewage treatment. It is particularly useful in coal washeries in which coal washwater is admitted to a thickener to induce settlement of the very fine coal and gangue particles entrained in the washwater. Once it has been clarified the washwater may be recycled through the coal washery while the fines settled out of the washwater are disposed of into tailing dams or stockpiles.

The measurement of the rate of sedimentation of the particles may be carried out by any suitable means known in the art. One suitable means includes a light disposed on one side of the sample container and a photoelectric cell disposed in the path of the light on the other side of the sample container. A timer is actuated as soon as a sample reaches a desired level in the sample container and is stopped when the particles in the container have settled to a level which allows the light to pass through the container and the liquid therein sufficiently to be registered by the photoelectric cell. The rate of addition of the flocculant to the body of the liquid is controlled in accordance with an algorithm based on the time recorded on the timer.

The suction means may comprise an air pump or vacuum generator which creates a reduced pressure in the sample container by pumping air therefrom and is electronically controlled. It could however comprise a mechanical piston adapted to move in a cylinder in fluid communication with the sample container to control the air pressure therein. The suction means and the sample container must be so constructed that the reduced pressure in the sample container above the sample may be maintained such that there is no unacceptable change in the level of the liquid in the sample container throughout the determination of the sedimentation rate.

BRIEF DESCRIPTION OF THE DRAWINGS

Hereinafter given by way of example only is a preferred embodiment of the invention describe with reference to the accompanying drawings in which.

Figure 1:
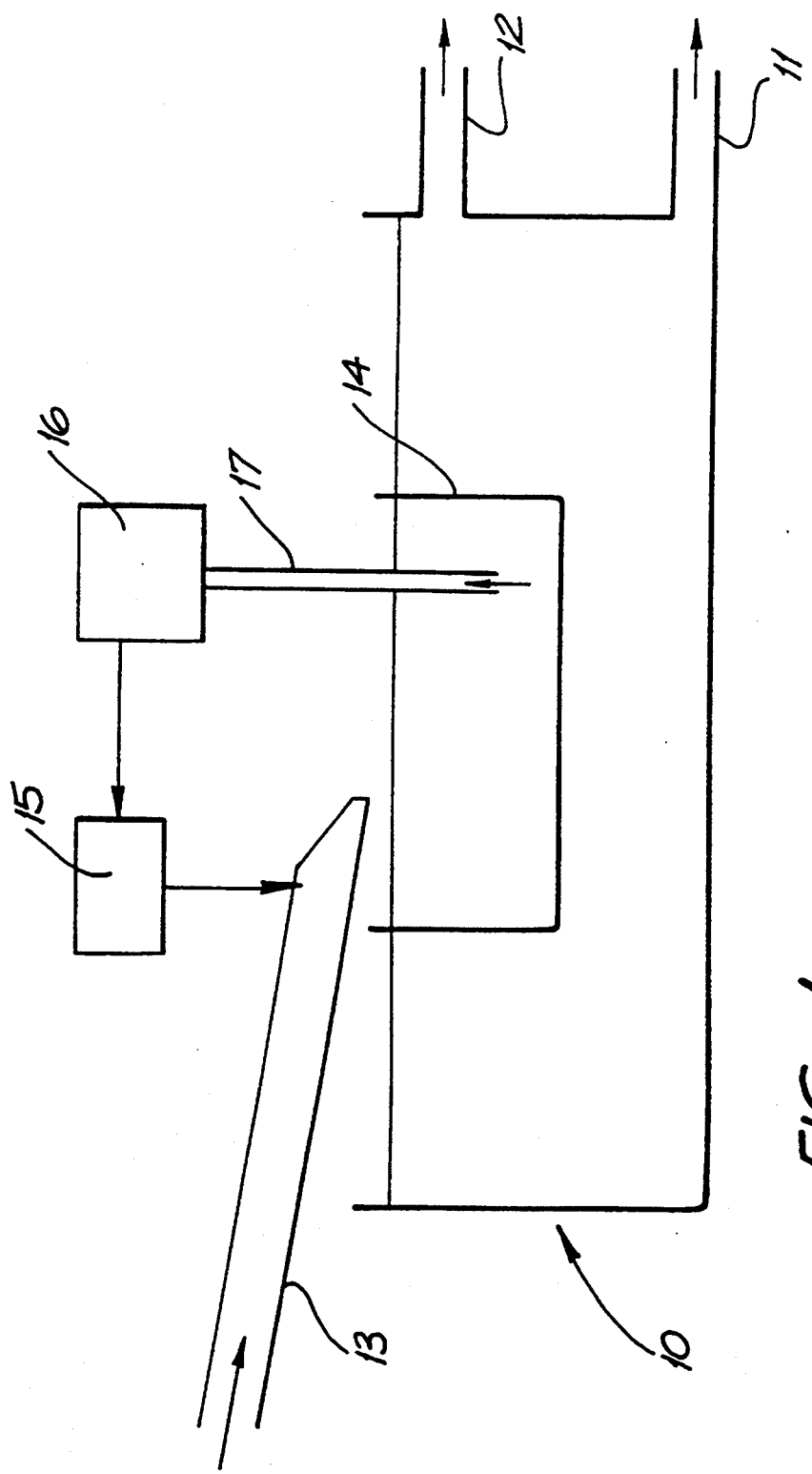
FIG. 1 is a diagrammatic presentation of a coal washery thickener fitted with a device according to the present invention.

As is shown in FIG. 1 a coal washery thickener includes a tank 10 having a lower outlet 11 for particulate slurry underflow and an upper outlet 12 for clean water overflow. Dirty washwater is delivered through a chute 13 into a ,central well 14 disposed in the middle of the tank 10. The dirty washwater contains fine particles of coal and gangue which may be clay or sand. A flocculant is metered into chute 13 from a flocculant supply device 15 to mix with the coal washwater. The flocculant causes the particulate matter in the washwater to flocculate and settle in the thickener. The clarified water is drawn from the tank 10 through upper outlet 12 and recycled through the coal washery. The settled flocculated particulate material is drawn out of the thickener through the lower outlet 11.

Figure 2:
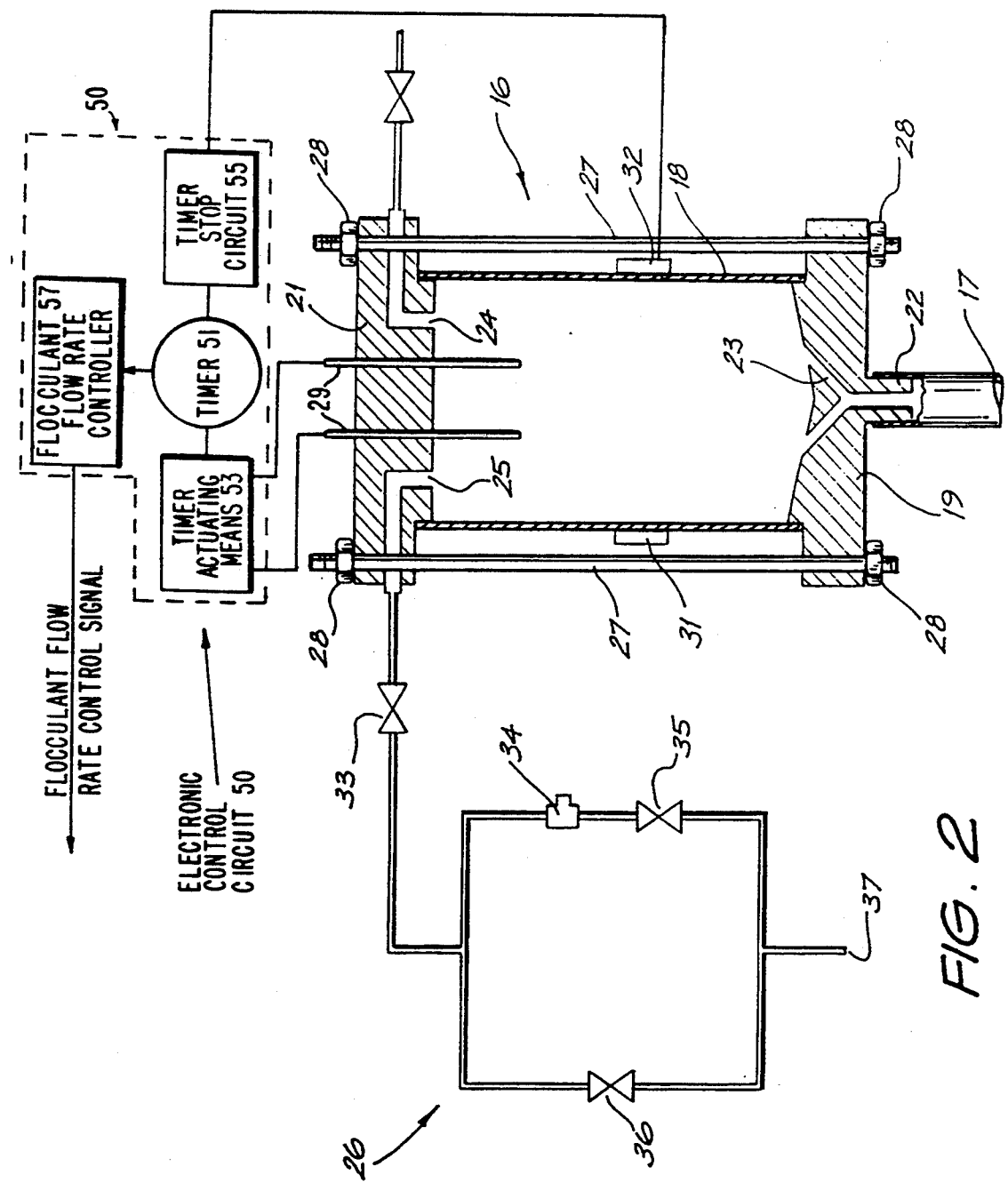
FIG. 2 is a diagrammatic representation of the sample container and associated suction means of the device according to the present invention shown in FIG. 1.

The addition of flocculant from the flocculant supply device 15 is controlled by a sedimentation testing device 16 shown in detail in FIG. 2. The device 16 draws a sample of the washwater from the centre well 14 of the thickener 10 through an inlet tube 17 which extends downwardly from the device 16 into the washwater. The rate of sedimentation of the particulate matter in the washwater is determined, as will be hereinafter described in more detail, and this data is used in an electronic control circuit 50 forming part of device 16 to control the rate of addition of the flocculant by the flocculant supply device 16 to the washwater. In this way sufficient flocculant is added to induce effective flocculation and settlement of the particulate matter in the washwater while avoiding the use of the excessive amounts of flocculant.

The sedimentation device 16 comprises a glass sample receiving cylinder 18 having a lower end plate 19 sealingly engaged with its lower end and an upper end plate 21 sealingly engaged with its upper end. The lower end plate 19 is formed with a spigot 22 to which the inlet tube 17 is connected. The inlet tube 17 is in fluid communication with the interior of the sample receiving cylinder 18 through a Y-shaped bore 23. The lower single arm of the bore 23 opens into its diverging upper arms so that if liquid is drawn rapidly into the sample cylinder it will splash against the wall of the cylinder 18 rather than spray up against the underside of the upper end plate 21 which, as will be explained subsequently, carries height probes the operation of which could be disrupted if they were sprayed with inflowing sample liquid.

The upper end plate 21 includes a clean water inlet duct 24 connected to a clean water supply so that the inside of the sample receiving cylinder can be washed after each sampling cycle. It also includes an air passage 25 connected to an air pressure regulating circuit 26. The upper and lower end plates 21 and 19 are held in position on the ends of the sample receiving cylinder 18 by clamping rods 27 and corresponding locking nuts 28 spaced around the periphery of the cylinder 18.

A pair of height probes 29 extend downwardly through the upper end plate 21 into the interior of the sample receiving cylinder 18, These probes are connected to the electronic control circuit and detect the rise of the liquid sample in the cylinder 18 up to the level of the probes 29. A light 31 is positioned on the outside of the cylinder 18 and is arranged to direct a beam of light through the cylinder 18 towards photoelectric cell 32 positioned on a diametrically opposite side of the cylinder 18.

The air pressure regulating circuit 26 includes a sealing solenoid valve 33, a vacuum generator 34, a vacuum solenoid valve 35, a purging solenoid valve 36 in parallel with the vacuum generator 34 and the valve 35, and a compressed air supply 37.

In operation a sampling cycle commences with the purging solenoid valve 36 and the sealing solenoid valve 33 being energised so that compressed air flow through the sample receiving cylinder 18 and the inlet tube 17 to purge any liquid from the inlet tube 17 so that only a fresh sample of the liquid will be drawn into the cylinder 18 as the cycle progresses.

The purging solenoid valve 36 is then closed and the vacuum solenoid valve 35 is opened. This enables the vacuum generator 34 to lower the pressure in the cylinder 18 thereby drawing a sample up the tube 17 into the cylinder 18. When the liquid reaches the level of the height probes 29 the sealing solenoid valve 33 is closed. The sample is now held in the sample receiving cylinder 18 by the reduced pressure induced therein by the vacuum generator 34.

As the liquid in the cylinder 18 reaches the height probes 29 a timer 51 is started by a timer actuating means 53 connected to the height probes 29, which is part of the electronic control circuit 50, and the light 31 is actuated. The particulate material in the sample in the cylinder 18 renders the liquid sample opaque. The beam from light 31 is therefore not registered by the photoelectric cell 32. As the particulates in the liquid sample settle the upper level of the opaque particles drops below the light 31. The beam from the light 31 then strikes the photoelectric cell 32 which is connected with a timer stop circuit 55 of the electronic control circuit 50 which sends a stop signal which stops the timer. The electronic control circuit 50 uses this timer-measured time in an algorithm to produce an output signal in a flocculent flow rate controlling circuit 57. This output signal is sent to the flocculant supply means 15 which responds by either increasing or decreasing the quantity of flocculant entering the dirty washwater in chute 13.

The reduced pressure above the sample in the cylinder 18 is maintained by the sealing solenoid valve 33 throughout the timing cycle. A predetermined time after the photoelectric cell has been actuated the sealing solenoid valve 33 and the purging solenoid valve 36 are opened purging the old sample from the cylinder 18. The flow of clean water through duct 24 is now briefly actuated to clean the cylinder 18 and the cycle is completed.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. A device for the determination of the rate of sedimentation of particles in a sample of a liquid and controlling the addition of a flocculant to the liquid in accordance with the rate of sedimentation so determined, the device comprising a sample container, an inlet duct in fluid communication with the sample container and extending downwardly from a lower end thereof and adapted to extend into a body of liquid to be sampled, suction means in fluid communication with an upper end of the sample container and adapted to create a reduced pressure in the sample container such that a sample of the liquid is drawn into the sample container, means to measure the rate of sedimentation of particles in the liquid sample, flocculant addition means adapted to add flocculant to the body of liquid from which the sample was drawn and means adapted to control the addition of flocculant from the flocculant addition means into the body of liquid in accordance with the rate of sedimentation of the particles in the liquid sample, the device being characterised in that the sample container and the suction means are adapted to hold the sample within the sample container, while the rate of sedimentation of the particles is determined, solely by maintenance of the reduced pressure in the sample container above the liquid sample.

2. The device of claim 1 wherein the sample container comprises a glass sample receiving chamber having an upper and lower end and wherein a lower end plate sealingly engages with the lower end and an upper end plate sealingly engages with the upper end, the lower end plate being formed with a spigot to which the inlet duct is connected.

3. The device of claim 2 wherein the inlet duct is in fluid communication with the interior of the sample container through a Y-shaped bore.

4. The device of claim 1 wherein the suction means comprises an electronically controlled air pump or vacuum generator.

5. The device claim 1 wherein the means to measure the rate of sedimentation of particles in the liquid sample comprises an electronic control circuit in connection with height probes located in the sample container and a photoelectric cell device.

6. The device of claim 5 wherein the photoelectric cell device includes a light source disposed on one side of the sample container and a photoelectric cell disposed in the path of the light on the other side of the sample container, and the electronic control means includes a timer.

7. The device of claim 6, wherein the electronic control means includes means for actuating the timer when the height probes detect a predetermined level of the liquid sample in the sample container and means for stopping the timer when the particles in the liquid sample in the sample container have settled to an extent that allows light to pass through the sample container and the liquid sample and register on the photocell.

8. A process for controlling sedimentation of particles in a body of a liquid, said process comprising the steps of drawing a sample of the liquid into a sample container through an inlet duct in fluid communication with a lower end of the sample container and with the body of the liquid by producing a reduced pressure in the sample container, determining the rate of sedimentation of particles in the sample, controlling the addition of flocculants from a flocculants addition means into the body of the liquid in accordance with the rate of sedimentation of the particles in the sample, and retaining the sample in the sample container throughout the determining of the sedimentation rate of the particles in the sample solely by maintaining the reduced pressure in the sample container above the sample.

* * * * *